United States Patent [19]

Sadée

[11] Patent Number: 6,007,986
[45] Date of Patent: *Dec. 28, 1999

[54] METHODS FOR ANTI-ADDICTIVE NARCOTIC ANALGESIC ACTIVITY SCREENING

[75] Inventor: Wolfgang Sadée, Ross, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/703,637

[22] Filed: Aug. 27, 1996

Related U.S. Application Data

[63] Continuation-in-part of application No. 08/261,500, Jun. 16, 1994, abandoned, which is a continuation-in-part of application No. 08/081,612, Jun. 23, 1993, abandoned.

[51] Int. Cl.⁶ .............................. C12Q 1/42; C12Q 1/68; G01N 33/53
[52] U.S. Cl. .............................. 435/6; 435/7.2; 435/7.21; 435/21
[58] Field of Search .................................. 435/7.2, 7.21, 435/6, 21

[56] References Cited

U.S. PATENT DOCUMENTS 5,061,715  10/1991  Sunkara et al. .......................... 514/314

OTHER PUBLICATIONS

Biedler et al., "Morphology and Growth, Tumorigenicity, and Cytogenetics of Human Neuroblastoma Cells in Continuous Culture," *Cancer Res.*, 33, pp. 2643–2652 (1973).

Costa et al., "Drug Efficacy at Guanine Nucleotide–Binding Regulatory Protein–Linked Receptors: Thermodynamics Interpretation of Negative Antagonism . . . ," *Molec. Pharmacol.*, 41, pp. 549–560 (1992).

Frey et al., "A $\mu$–Opioid Receptor in 7315c Tumor Tissue Mediates Inhibition of Immunoreactive Prolactin Release and Adenylate Cyclase Activity," *Endocrin.*, 115, pp. 1797–1804 (1984).

Kogan et al., "Elevated Basal Firing Rates and Enhanced Responses to 8–Bromo–cAMP in Locus coeruleus Neurons in Brain Slices from Opiate Dependent Rats," *Eur. J. Pharmacol.*, 211, pp. 47–53 (1992).

Nestler, "Molecular Mechanisms of Drug Addiction," *J. Neurosci.* 12:7, pp. 2439–2450 (1992).

Rasmussen et al., "Opiate Withdrawal and the Locus coeruleus: Behavioral, Electrophysiological, and Biochemical Correlates," *J. Neurosci.*, 10, pp. 2308–2317 (1990).

Sibinga et al., "Opioid Peptides and Opioid Receptors in Cells of the Immune System," *Ann. Rev. Immunol.*, 6, pp. 219–249 (1988).

Yu et al., "A Human Neuroblastoma Cell Line Expresses $\mu$ and $\delta$ Opioid Receptor Sites," *J. Biol. Chem.*, 261, pp. 1065–1070 (1986).

Yu et al., "Efficacy and Tolerance of Narcotic Analgesics at the $\mu$ Opioid Receptor in Differentiated Human Neuroblastoma Cells," *J. Pharmacol. Exp. Ther.*, 245, pp. 350–355 (1988).

Yu et al., "Differentiation of Human Neuroblastoma Cells: Marked Potentiation of Prostaglandin E–Stimulated Accumulation of cAMP by Retinoic Acid," *J. Neurochem.*, 51, pp. 1892–1899 (1988).

Yu et al., "Regulation of Cyclic AMP by the $\mu$–Opioid Receptor in Human Neuroblastoma SH–SY5Y Cells," *J. Neurochem.*, 55:4, pp. 1390–1396 (1990).

Schütz et al., "Reverse Intrinsic Activity of Antagonists of G Protein–Coupled Receptors," *TiPS*, 13 (Oct. 1993), pp. 376–379.

Chen et al., "Moleculare Cloning and Functional Expression of a $\mu$–Opioid Receptor from Rat Brain," *Molecular Pharmacology*, 44, pp. 8–12 (1993).

Wang et al., "Constitutive $\mu$ Opioid Receptor Activation as a Regulatory Mechanism Underlying Narcotic Tolerance and Dependence," *Life Sciences*, 54:20, pp. 339–350 (1994).

Smith et al., "Problems and Approaches in Studying Membrane Opioid Receptors," *Molecular Approaches to Drug Abuse Research Volume I*, edited by Lee et al., U.S. Dept. of Health & Human Services, pp. 69–84 (1991).

Hawkins et al., "[³H]–[H–D–Phe–Cys–Try–D–Trp–Orn–Thr–Pen–Thr–NH₂] ([³H]CTOP), A Potent and Highly Selective Peptide for Mu Opioid Receptors in Rat Brain," *J. Pharmacol. & Exp. Ther.*, 248:1, pp. 73–80 (1989).

Abdelhamid et al., "Characteristics of $\mu$ and $\delta$ Opioid Binding Sites in Striatal Slices of Morphine–Tolerant and –Dependent Mice," *Eur. J. Pharmacol.*, 198, pp. 157–163 (1991).

(List continued on next page.)

*Primary Examiner*—Anthony C. Caputa
*Assistant Examiner*—Robert C. Hayes
*Attorney, Agent, or Firm*—Majestic, Parsons, Siebert & Hsue

[57] ABSTRACT

The present invention provides assays to measure the regulation of the narcotic analgesic addictive state. Practice of the invention permits classification of test compounds for their effects on an activated opioid $\mu$ receptor state. When opioid $\mu$ receptor cells are treated with a test composition under investigation, then in one embodiment the propensity of the test composition to elicit a spontaneous cAMP overshoot and an inverse agonist induced cAMP overshoot is determined and serves as a surrogate measure of addiction liability. The inverse agonist induced cAMP overshoot signifies the presence of what is designated as the constitutively active state for the opioid $\mu$ receptors. The use of these assays has led to the identification of compounds that have the desired effects on the constitutive activation of the opioid $\mu$ receptors. The therapeutic potential of these compounds include treating patients who are addicted to a narcotic analgesic or who have taken an overdose of a narcotic analgesic, or whose pain is being relieved with a narcotic analgesic.

5 Claims, 3 Drawing Sheets

OTHER PUBLICATIONS

Sharma et al., "Dual Regulation of Adenylate Cyclase Accounts for Narcotic Dependence and Tolerance," *Proc. Antl. Acad. Sci. USA*, 72:8, pp. 3092–3096 (1975).

Sadée et al., "Constitutive Activation of the µ–Opioid Receptor: A Novel Paradigm of Receptor Regulation in Narcotic Analgesia, Tolerance, and Dependence," *Analgesia*, 1:1, pp. 11–14 (1994).

Lameh et al., Abstract of "Agonist Induced Conversion of the Hml Muscarinic Cholinergic Receptor to a Constitutively Active State: A Novel Papadigm of Receptor Regulation," p. 47 of the program for *Subtypes of Muscarinic Receptors: The Sixth International Symposium*, Sponsored by Boston University School of Medicine and Johann Wolfgang–Goethe University, held in Fort Lauderdale, Florida, Nov. 9–12, 1994.

Baker, Mitzi, "New Hypothesis on How Narcotics Produce Tolerance, Dependency," *Synapse* (newspaper of the University of California, San Francisco), 39:15 (Jan. 12, 1995), pp. 1 and 5.

Högger et al., "Activating and Inactivating Mutations in N–and C–terminal i3 Loop Junctions of Muscarinic Acetylcholine Hm1 Receptors," *J. Biol. Chem.*, 270:13, (1995), pp. 7405–7410.

Wang et al., "Agonist Induced Constitutive Activation of the µ Opioid Receptor by Phosphorylation" *Regulatory Peptides*, 54:1, (1994), pp. 323–324.

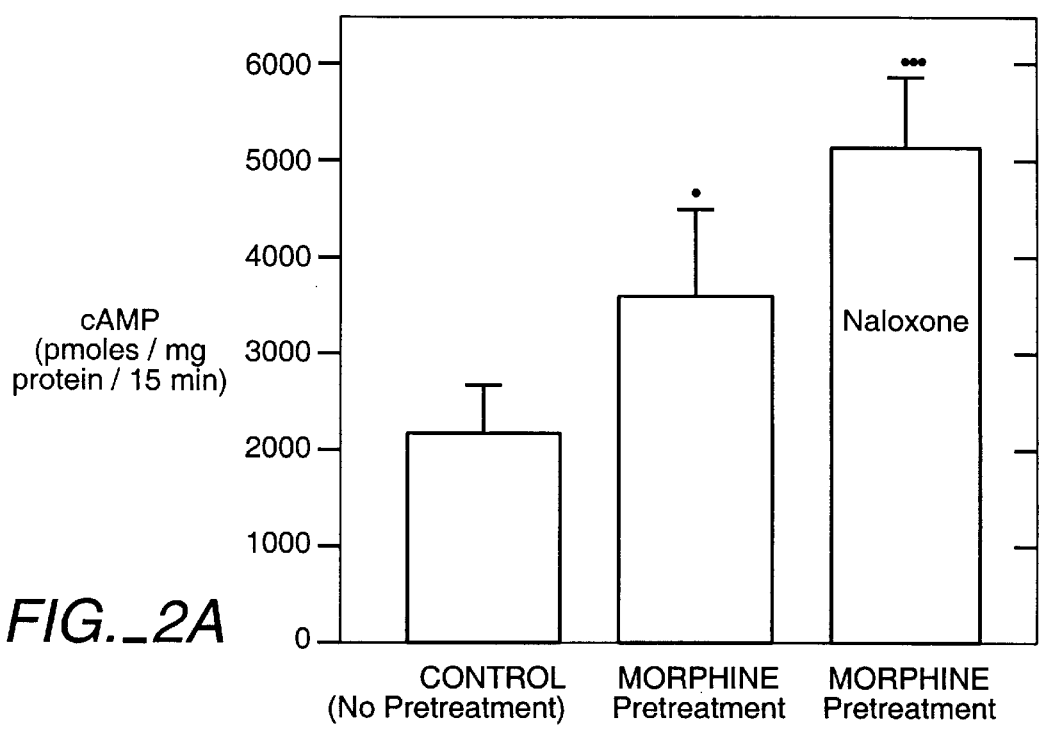
FIG._2A
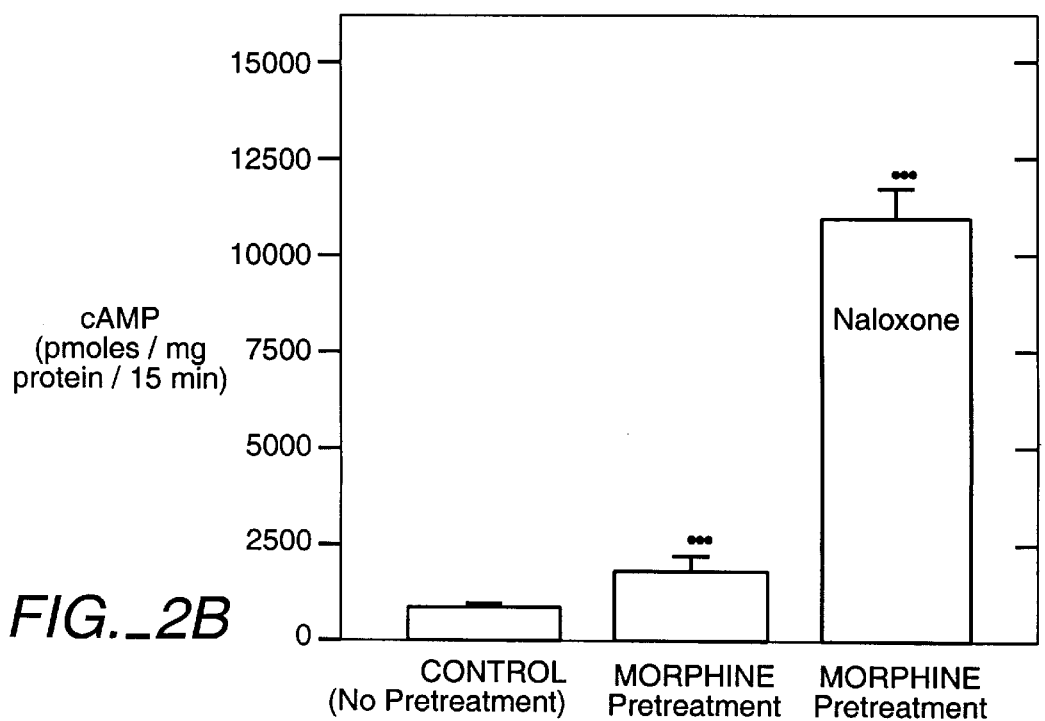
FIG._2B

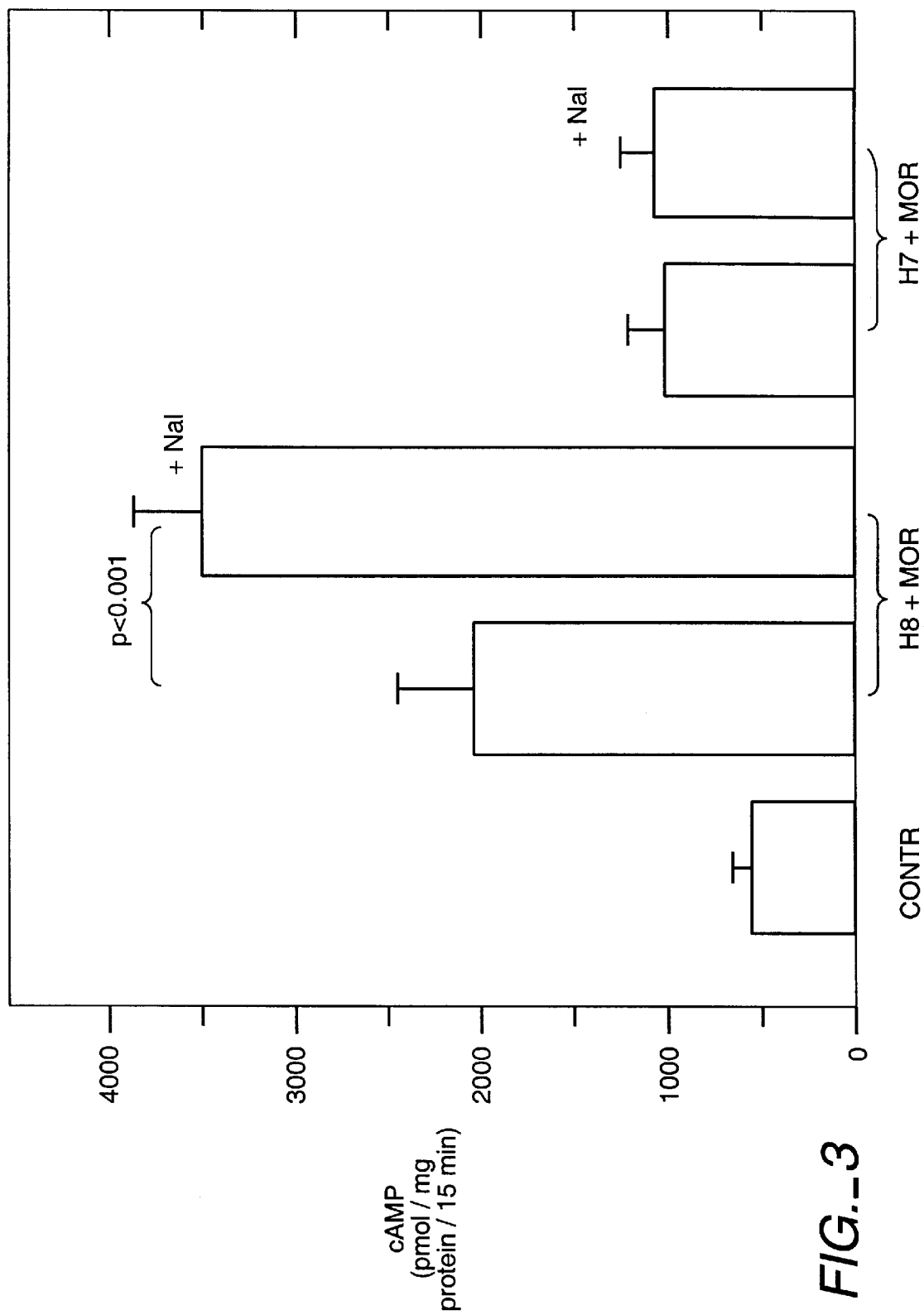
FIG._3

METHODS FOR ANTI-ADDICTIVE NARCOTIC ANALGESIC ACTIVITY SCREENING

This is a continuation-in-part of Ser. No. 08/261,500, filed Jun. 16, 1994, now abandoned, which was a continuation-in-part of Ser. No. 08/081,612, filed Jun. 23, 1993, now abandoned, all of common assignment herewith.

This invention was made with Government support under Grant No. DA 04166, awarded by the U.S. Department of Health and Human Services. The Government has certain rights in this invention.

FIELD OF THE INVENTION

The present invention generally relates to screening for the pharmacological activities of narcotic drugs, and more particularly relates to assays useful in classifying the narcotic activity of compounds and treatments using anti-addictive agents determinable from such assays.

BACKGROUND OF THE INVENTION

Endogenous opiate receptors were discovered in the 1970s, and have been intensely studied in seeking the mechanisms by which particular drugs lead to addiction. However, in his 1992 review of molecular mechanisms of drug addition, Nestler noted that such mechanisms have remained elusive. *J. Neurosci.*, 12 (7), pp. 2439–2450 (1992).

A number of different opioid receptor types have been identified. Among the known receptor types is the opioid $\mu$ receptor.

Narcotic analgesics act at the opioid $\mu$ receptor to produce analgesia. However, continued use of narcotic analgesics typically leads to habituation or addiction, and use of one leads to cross-tolerance/dependence for the others. Despite their therapeutic uses, because patients develop increasing tolerances to the narcotic analgesics, increasing doses are required to achieve relief from pain. Undesirable side effects then tend to develop, such as physical dependence.

Illustrative narcotic analgesics are, for example, the various alkaloids of opium such as morphine, morphine salts (such as morphine hydrobromide, morphine hydrochloride, morphine mucate, morphine oleate, and morphine sulfate), and morphine analogs such as normorphine, diacetyldihydromorphine, codeine, and diacetylmorphine (heroin). Other widely used narcotic analgesics include methadone, meperidine, levorphanol, propoxyphene, fentanyl, oxymorphone, anileridine, metopon, and pentazocine.

The agonistic actions and dependence-producing properties of narcotic analgesics can be, and are, studied in various mammalian species besides humans, since practical and governmental considerations frequently require that studies be first done in small rodents and/or monkeys before the analgesic properties of pharmaceuticals are tested with humans. Drugs that have morphine-like properties in mammals other than humans have been found to be morphine-like in humans, and a variety of analgesic assays has been developed with animals which have gained widespread acceptance for predicting properties in humans. Biochemical changes during long term narcotic exposure can be studied in target tissues, such as the locus coeruleus (LC) of the rat, which is a good model of opiate dependency. Thus, upon chronic opiate treatment, researchers have demonstrated that LC neurons develop tolerance to the acute inhibitory actions of opiates, and in parallel chronic treatment causes a dramatic upregulation of the cAMP second messenger system at every major step between receptor and physiological response, which leads to a dependent state. See, for example, Nestler at 2440.

To date, assays of the $\mu$ opioid receptor system have been unable to detect any major changes of that system during narcotic addiction. Thus, much of the current work has focused on events downstream of the receptor, such as long-term gene regulation, in attempting to account for the dependent state. Because the dependence liability of narcotic drugs severely limits their clinical utility as potent analgesics and exerts a heavy toll on society through illicit narcotic drug use, a screen for agents that could prevent or reverse the narcotic dependent state or might facilitate gradual withdrawal would greatly enhance the clinical utility of narcotic analgesics and could serve as an effective pharmacological weapon in the fight against illicit drug use.

SUMMARY OF THE INVENTION

A novel mechanism is proposed where opioid $\mu$ receptor exposure to agonist leads to constitutive activation of those receptors. It is through this mechanism that the addictive state to narcotic analgesics is regulated.

One aspect of the present invention is to provide a means for assaying or measuring the regulation of the addictive state, in the search for compounds that prevent or reverse constitutive $\mu$ receptor activation, and to classify test compounds for their effects on the constitutively active $\mu$ receptor state.

Other aspects of the present invention are methods for treating patients who are addicted to a narcotic analgesic, or who have taken an overdose of a narcotic analgesic, or whose pain is being relieved with a narcotic analgesic. Therapeutic methods in accordance with the invention normally involve selection of an agent with desired effects on the constitutive activation of opioid $\mu$ receptors. These desired effects are determinable from the inventive assays.

Accordingly, practice of the invention is expected greatly to enhance the clinical utility of narcotic analgesics and to serve as effective pharmacological weapons in the fight against illicit drug use.

BRIEF DESCRIPTION OF THE DRAWINGS

FIGS. 2 A–B graphically illustrates two different types of cells stably transfected with the $\mu$ opioid receptor in accordance with the invention; and, FIG. 3 graphically demonstrates how practice of the invention may be applied.

DETAILED DESCRIPTION OF THE PREFERRED EMBODIMENTS

Figure 1:
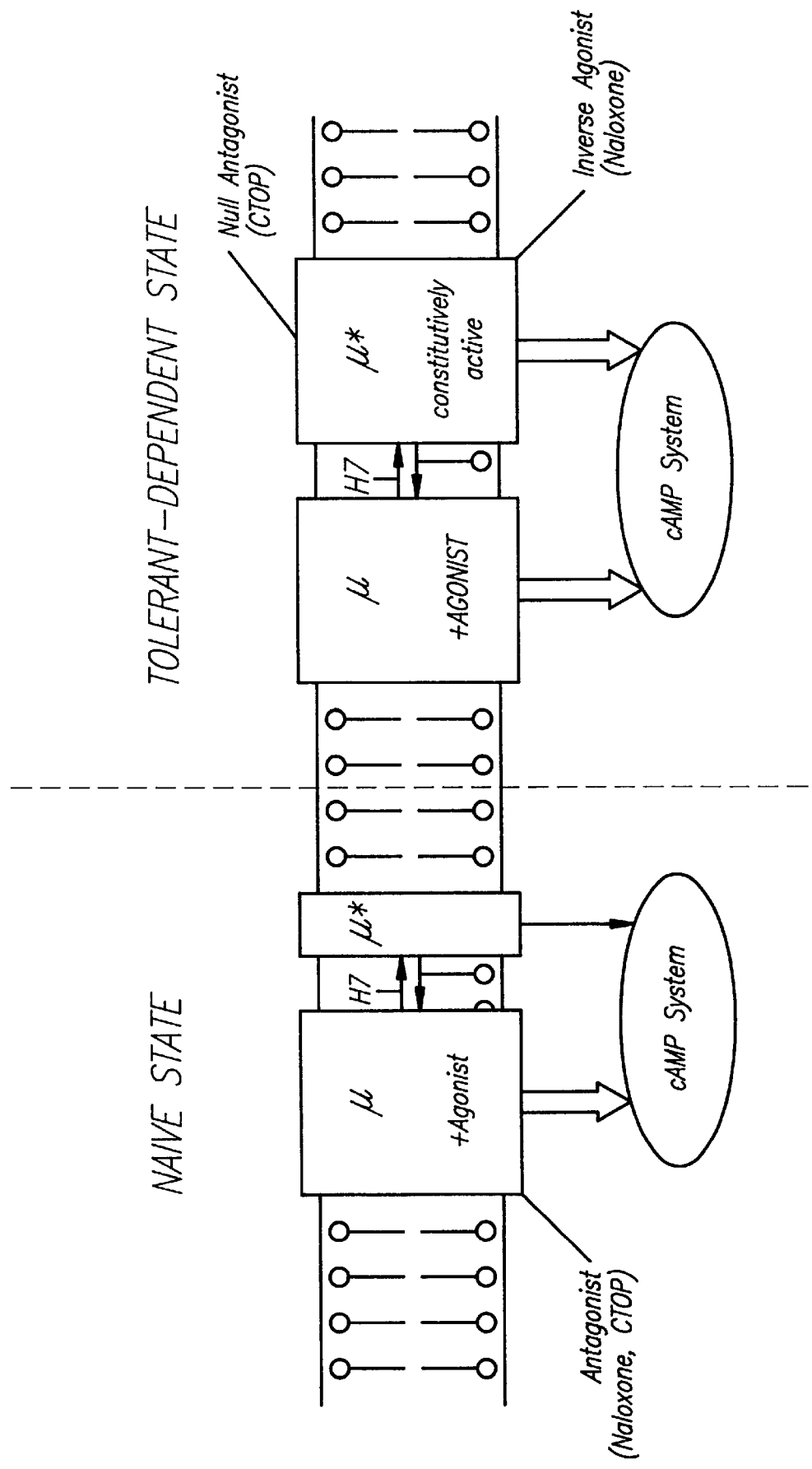
FIG. 1 is a schematic representation of relationships useful in understanding the tolerant dependent state.

An aspect of the present invention is to screen or classify test compounds with $\mu$ receptor activity for their effect on the constitutively active receptor. In order to practice the invention, effects on cAMP can be used as markers in one inventive embodiment.

Although the use of cAMP values is a preferred embodiment of the invention as indicia for determining opioid $\mu$ receptor activity, other effects and markers are also contemplated as being useful.

With reference to FIG. 1 and when using cAMP values as indicia for opioid $\mu$ receptor activity, the constitutively active μ receptor is illustrated as "μ*." That is, the μ* receptor represents the constitutively active state of the μ opioid receptor, whereas μ is the receptor in its resting state which is sensitive to stimulation by agonists. The cAMP system consists of a second messenger cascade with G proteins, adenylyl cyclase, and protein kinase A. Activated μ receptors generally inhibit the cAMP system, and the size of the arrows indicates the relative strength of this inhibition. In the naive state (no prior drug exposure), the activity of the μ* state is minimal, and most receptors are drug sensitive. For purposes of illustration, morphine serves as a prototypal agonist, and naloxone (and CTOP also, as will be discussed hereinafter) as a classical antagonist, i.e., with no action by themselves but effective in blocking the agonist's effect on the resting μ state.

During development of the dependent state resulting from narcotic agonist pretreatment, a substantial upregulation of the cAMP system occurs, leading to a cAMP overshoot upon removal of the agonist (here referred to as "spontaneous cAMP overshoot"). In parallel, a slow net conversion of μ to μ* occurs, so that there are fewer μ receptors remaining sensitive to the action of agonists, as one mechanism leading to tolerance. Further, the increased abundance of the μ* state is essential to compensate for the upregulated cAMP system, to maintain close to normal cAMP levels. Hence, the hallmark of the tolerant-dependent state is the combination of the increased μ* activity and the upregulated cAMP system. Naloxone is shown in FIG. 1 to act as an inverse agonist, i.e., it blocks the μ* activity. Hence, the addition of naloxone to drug-free, tolerant-dependent tissue leads to an increased cAMP overshoot (here referred to as "naloxone cAMP overshoot"). In contrast, CTOP acts at the active μ* receptor as a neutral or null antagonist by binding to μ* without affecting activity.

In describing practice of this invention, a source of opioid μ receptors in combination with a means of monitoring constitutively active μ receptors, such as a cAMP system, will together sometimes hereinafter be termed the "biological system." A preferred source of opioid μ receptors that are exposed to or coupled with cAMP production is a human neuroblastoma (NB) cell line (SK-N-SH) and its NB subclone SH-SY5Y, both which express abundant μ opioid receptors (about 50,000 sites per cell). When intact cells are grown under appropriate cell culture conditions, the cells will be producing cAMP. Another source of a useful biological system for purposes of this invention can be certain tissues from experimental animals (e.g. rats and mice, which are good models for opioid μ receptor activity in humans), such rat locus coeruleus or guinea pig ileum.

When whole cells are used as the biological system, then it is desirable to add an adjuvant or stimulating agent of adenylyl cyclase, such as PGE, VIP, or forskolin, and to avoid phosphodiesterase inhibitors such as IBMX. NB cells are preferably first differentiated with, for example, 1–10 μM retinoic acid to enhance stimulatory and inhibitory receptor coupling to the cAMP system. Such preparations of a biological system have been described by Yu et al., J. Neurochem., 51, pp. 1892–1899 (1988); Yu et al., J. Neurochem., 55, pp. 1390–1396 (1990); and Yu and Sadée, J. Pharmac. Exp. Ther., 245, pp. 350–355 (1988).

When opioid μ receptor rich cells are treated with a test composition under investigation in accordance with the invention, then the propensity of the test composition to elicit the spontaneous and an inverse agonist induced cAMP overshoot can be determined and serve as a surrogate measure of addiction liability. The inverse agonist induced cAMP overshoot signifies the presence of constitutively active receptors.

In one variation of the assay, cells can be treated with a narcotic analgesic for 12 hours or longer to induce a dependent state, and then compounds or mixtures of compounds suspected as narcotic agonists or antagonists can be tested for their ability to mimic the inverse agonist induced cAMP overshoot or the agonist (e.g. morphine) caused depression of cAMP levels in the moderately tolerant cells. Control values are determined by measuring the effects of the receptors on cAMP production in the absence of agonist induced opioid μ receptor activity.

Test compounds that appear by themselves to have no effect on cAMP levels in drug free agonist pretreated-dependent cells should nevertheless then be tested in combination with either the agonist or the inverse agonist, in order to locate null antagonists. Compounds determined to be null antagonists (i.e. blocking the effects of morphine or of both morphine and naloxone with no effect when given alone) have the potential for treating overdoses of narcotic analgesics while avoiding the risk of excessive precipitated withdrawal, or they may serve to discourage additional drug uses by selectively blocking acute drug effects, with minimal long term effects (such as possible overall μ receptor upregulation by inverse agonists).

To summarize, one aspect of the present invention is an assay useful in screening for effects on opioid μ receptor activity. The assay can be performed by means of a kit that includes or is used in combination with a cAMP system. For example, when a cell line such as the SK-N-SH is used, then the cell line is capable of producing cAMP under cell growth conditions and is rich in opioid μ receptors. A first cAMP value is determined by measuring the effects of a first portion of these receptors on cAMP production in the absence of agonist induced opioid μ receptor activity. This first cAMP value acts as a control value, and preferably is to be performed, but is not necessary. Second and third cAMP values are also determined. The second cAMP value is determined by measuring the effects of a second portion of receptors on cAMP production while the receptors are in a constitutively active state but are substantially free of agonist molecules. The third cAMP value is determined by measuring the effects of the third portion of the receptors on cAMP production while they are in a constitutively active state, are substantially free of any agonist molecules, and are in the presence of a sufficient quantity of an inverse agonist to associate inverse agonist molecules with substantially all the receptors. In determining the third cAMP value, it is preferred to use as high a concentration as feasible to associate inverse agonist molecules with substantially all the receptors, in order to achieve maximal effects (e.g. the highest cAMP overshoot).

The difference between the second cAMP value and the third cAMP value represents activity of the receptors. By "substantially free" of agonist molecules (in determining the second and third cAMP values) is meant there is less than about one percent of the total agonist drug remaining after pretreatment with a near maximally effective dose so that there would be no measurable effect in response curves. One can make the removal determinations through use of radio-immune assays or can look at the wash water by using the wash water to expose naive cells and determining by bioassays whether there is an effect. Typically by washing cells carefully three times, the substantial removal is accomplished if the agonist is morphine at 1 μM. If one is performing the assay in vivo, then the tissue is removed, sliced, and is washed in a water bath.

A variation of the assay permits the search for test compositions that prevent or decrease the formation of the constitutively active μ receptor state without affecting pharmacological potency. Such agents can be added to the opioid μ receptors during narcotic agonist incubation (to produce a constitutively active state) or after removal of the narcotic agonist, to test whether the overshoot induced by an inverse agonist can be reversed more rapidly. This class of test compounds has the potential to prevent or reverse the generation of constitutively active receptors and thus has the potential (when used therapeutically with a narcotic analgesic) to suppress the addictive liability of the narcotic analgesic, or may be useful by itself as an agent in treating narcotic drug addiction. Several such compounds (H7, H9, and HA-1004) have been identified using the proposed screen. In addition, H7 (1-(5-isoquinolinesulfonyl)-2-methylpiperazine dihydrochloride) has been shown to reverse the tolerant-dependent state of morphine-injected mice to a native state, demonstrating the therapeutic potential of this class of compounds.

Recent evidence suggests that the constitutively active μ receptor state is formed by the phosphorylation of the μ receptor by a novel kinase activity (μ kinase). Thus, H7 and other such compounds are likely to be μ kinase inhibitors with other possible therapeutic uses. Moreover, an alternative method for screening for agents that prevent and/or reverse the formation of the constitutively active μ receptor state is described by Wang et al., *FEBS Letters*, 387, pp. 53–57 (1996).

If cell membranes are the source of the desired biological system, then one typically will use the same or similar pretreatments noted above, but will perform cAMP assays in vitro with the cell membranes.

Practice of the invention is generally useful in determining effects on opioid μ receptor activity, such as whether test compounds having opioid μ receptor activity would interact with the constitutively active μ receptor, or whether test compounds prevent or reverse the constitutively active μ receptor state. Practice of the invention permits classification of the ligand as a full inverse agonist, a partial inverse agonist, or a partial agonist. In addition, one can determine whether a test compound is a null (or neutral) antagonist.

By "full inverse agonist" is meant an agent that suppresses completely the effects of the constitutively active μ receptor state.

By "partial inverse agonist" is meant an agent that at maximal dosages suppresses only partially the effects of the constitutively active μ receptor state.

By "partial agonist" is meant an agent that at maximal dosages causes only partial activation of the resting, drug-sensitive μ receptor state.

By "null, or neutral, antagonist" is meant the compound simply binds to the receptor without changing its activity. A null antagonist may bind selectively to the resting, drug-sensitive μ receptor state, or to the constitutively active μ receptor state, or to both states.

Once agents are classified by means such as the inventive assay, optimal characteristics for treating drug addiction can be obtained in standard animal tests in vivo.

As will be further exemplified hereinafter, these classifications may be performed by determining certain cAMP values as reference points against which the cAMP effects of the test compound or composition are compared. That is, the first, second, and third cAMP values previously noted are used to classify the test compound or composition.

Receptors may show a certain minimal basal activity in the absence of agonist, and agonist exposure is usually thought to result in desensitization (e.g., by phosphorylation), and hence tolerance to a drug. However, it is proposed here that agonist exposure of neurotransmitter receptors leads to constitutive activation, which no longer depends on the presence of an agonist. As the cAMP system becomes upregulated to compensate for the inhibitory influence of narcotics, the μ receptors become increasingly activated constitutively, i.e., no longer requiring an agonist. Thus, the μ* receptors and the enhanced cAMP system balance each other out, when one assumes this type of activation occurs with the μ opioid receptor, many tolerance and dependence phenomena can be accounted for.

In cases where receptors are constitutively active, one distinguishes between agonists which further stimulate the remaining inactive receptors, and inverse agonists, which return the activated receptor to the inactive ground state. An example are the benzodiazepine receptors, where agonists are anxiolytic whereas inverse agonists are anxiogenic. Applied to the constitutively activated μ receptor in the dependent state, it is predicted that an inverse agonist will increase cAMP levels by reversing the active μ* receptor state to the ground state. As will be further discussed below, naloxone is indeed such a reverse agonist, while it is also a classical antagonist of the resting, drug-sensitive μ receptor state.

Thus, for example, upon stimulation with morphine, the μ opioid receptors in SK-N-SH cells are gradually converted to a constitutively activated μ* form which no longer depends on the presence of agonist. Maximal constitutive activation is expected in the fully dependent state. After 12–48 hours pretreatment of SK-N-SH cells with 1 μM morphine, and the subsequent complete removal of the drug, then naloxone significantly increases $PGE_1$-stimulated cAMP accumulation, whereas no increase or even a decrease is observed in cells treated with morphine for only 20 minutes or less. Therefore, naloxone acts as an inverse agonist at the constitutively activated opioid receptor (EC50~3 nM). These results are consistent with the observation that with increasing morphine dependence in experimental animals, the doses of naloxone required to elicit withdrawal symptoms are greatly reduced because of an increase of receptors in the active μ* state.

With an upregulated cAMP system and a constitutively activated μ receptor, tolerance to narcotic agonists is expected because there are fewer receptors remaining to be activated. Further, one would expect lower doses of naloxone to precipitate withdrawal, because in the dependent state there are more activated receptors available for the inverse agonist to act on. Lastly, the decay of the activated μ receptor state would dictate the time course of withdrawal, rather than the rate of drug removal from the body. Residual constitutive receptor activity after the peak of withdrawal accounts for the continuing ability of naloxone to elicit overt withdrawal systems over a prolonged time period.

Such a constitutively activated μ opioid receptor mechanism goes beyond current hypotheses of narcotic addiction, and this mechanism lends itself to the discovery of agents that prevent or reverse constitutive activation, or that facilitate withdrawal by exhibiting the proper characteristics of a null antagonist or partial inverse agonist (to limit continued drug exposure without maintaining the dependent state nor causing excessive withdrawal). Hence, compounds previously classified as mixed agonist-antagonist or partial agonist narcotic drugs may display partial inverse agonism of potential utility in treating narcotic addiction. Knowledge of the mechanisms contributing to the regulation of the constitutively active receptor state could lead to diagnostic tests of individual drug dependence liability.

No compelling mechanism had been proposed previously that accounts for the driving force behind establishing and maintaining the narcotic dependent state. Even though an important role for the $\mu$ receptor in this process had long been speculated, experimental results have failed to reveal significant changes. Because the process of constitutive activation lends itself to screening anti-addictive agents and probing the molecular mechanisms of narcotic dependence, practice of the invention is expected to provide a new approach to separating the beneficial activity of narcotics from undesirable long term effects.

As earlier noted, the biological system being used for practicing the inventive assay can be pretreated, such as by treating cells with a narcotic analgesic for 12 hours or longer to induce a dependent state. The particular cell incubation and pretreatment conditions chosen will vary, with some relationships of treatment with cAMP determinations being summarized in Table 1.

TABLE 1

| Pretreatment → | Washout → | Recovery → | cAMP Assay → | CAMP Values |
|---|---|---|---|---|
| no drug | + | 0–120 minutes | no drug | First cAMP value (control) |
| morphine | + | 0–120 minutes | no drug | Second cAMP value (spontaneous cAMP overshoot) |
| morphine | + | 0–120 minutes | naloxone | Third cAMP value (naloxone cAMP overshoot) |

As suggested by Table 1, after the washout step and before the cAMP assay (with PGE1), a recovery incubation stage of up to about two hours (where no drug is present) can be used during which one can test for reversal of the constitutively active $\mu$ receptor state.

With reference to Table 1 and using the "first cAMP value," "second cAMP value," and "third cAMP value" terminology previously described: the "first cAMP value" is the control level in untreated cells, the "second cAMP value" represents the spontaneous cAMP overshoot which rapidly drops to the control value if a recovery period of 30 minutes or more is used, and the "third cAMP value" is the naloxone cAMP overshoot above the spontaneous cAMP overshoot, which represents the constitutively active $\mu^*$ state. The "third cAMP value" remains elevated for at least two hours if a recovery incubation is used.

Turning to FIG. 2, cAMP levels in SK-NS-H (subclone SH-SY5Y) neuroblastoma cells (FIG. 2A) and HEK293 cells stably transfected with the $\mu$ opioid receptor (FIG. 2B) are illustrated. The first control cAMP level was obtained in untreated cells, whereas the test cells were pretreated with 1 $\mu$M morphine for ~12 hours, followed by complete removal of the agonist. The second cAMP level was then obtained in the absence of any drug, and it represents the known spontaneous cAMP overshoot. The third cAMP level was obtained in the presence of 1 $\mu$M naloxone (IC50 1–3 nM). The difference between the second and third cAMP levels represents the naloxone-induced cAMP overshoot, indicative of the constitutively active $\mu^*$ receptor state.

FIG. 3 demonstrates how this inventive assay can be used to distinguish between an agent capable of preventing $\mu^*$ formation (H7) and an inactive compound (H8). In this experiment, either H7 or H8 (100 $\mu$M) were added to the preincubation medium containing morphine. After removal of the preincubation medium, the second and third cAMP levels were determined as in FIG. 2. Compound H7 abolished the naloxone-induced cAMP overshoot (no difference between the second and the third cAMP value), whereas H8 had no such effect. H7, but not H8, was subsequently found to reverse morphine tolerance and dependence in mice. (Note that H7 and H8 had some effects on the spontaneous cAMP overshoot induced by morphine pretreatment (second cAMP value). This however does not interfere with the evaluation of the naloxone-induced cAMP overshoot which relies on the difference between the second and the third cAMP values.)

Practice of the invention has already proven its utility by permitting identification of several representative compounds that prevent constitutive activation of the $\mu$ receptor, and has also led to the identification of null antagonists.

Another aspect of the present invention is as a method of treating a patient suspected of having taken an overdose of a narcotic analgesic. Thus, one selects an agent determined to be a null antagonist for the suspected narcotic analgesic. The null antagonist will preferably have been determined as such by using the inventive assay.

As will be illustrated by Example 2, the determination of a null antagonist then permits administering a selected null antagonist for the suspected narcotic analgesic in a pharmaceutically effective amount, which means that the dose administered preferably is effective to block narcotic agonist effects in addicted patients without inducing severe withdrawal in treating a narcotic overdose or when one initiates withdrawal treatment. This is advantageous over present practice wherein naloxone is typically administered to patients suspected of having taken an overdose of a narcotic analgesic, which plunges the patient into an immediate severe withdrawal.

The pharmaceutically effective amount of agents determined to be null antagonists will be readily determinable clinically by establishing safe dosages and a dose-response curve in blocking analgesia in any established clinical pain model. Analgesia in rodent animal models can be measured by the tail-flick method of D'Amour and Smith, *J. Pharmac. Exp. Ther.*, 72, pp. 74–79 (1941), and as modified by Tulunay and Takemori, *J. Pharmac. Exp. Ther.*, 190, pp. 395–400 (1974), both incorporated herein by reference. $ED_{50}$ values, their 95% confidence limits, and significance of potency ratio between two $ED_{50}$ values may be determined by the method of Litchfield and Wilcoxon, *J. Pharmac. Exp. Ther.*, 96 pp. 99–113 (1949), incorporated herein by reference.

Another aspect of the present invention is as a therapeutic method for treating a patient's pain. In this aspect of the present invention, an agent is determined to prevent constitutive activation of opioid receptors and/or to reverse constitutive activation of opioid $\mu$ receptors. This determination is preferably performed as will be described and exemplified by Example 1. The agent is then selected and administered in a therapeutically effective amount, such as in conjunction with a pain relieving amount of narcotic analgesic. That is, this aspect of the invention is directed to enhancing the clinical uses of narcotic analgesics because the agent selected prevents long term narcotic effects without blocking acute effects.

Alternatively, an agent shown to reverse constitutive $\mu^*$ receptor activation can be used to treat patients addicted to narcotic drugs. This agent would therefore remove the driving force of the dependent state and may thereby effectively treat narcotic addiction. Therapeutically effective amounts of the determined agents to be selected may be ascertained from dose-response curves in narcotic addicts where pretreatment with the agent would block subsequent naloxone induced withdrawal.

Aspects of the invention will now be further illustrated by specific examples, which are intended to exemplify the invention and not to be limited thereof.

EXAMPLE 1

Because receptor activity is generally regulated by phosphorylation, several known protein kinase inhibitors were tested for their ability to prevent and reverse the formation of the constitutively active $\mu$ receptor state in accordance with the invention, as follows.

The test compounds (10–100 $\mu$M) were first incubated with SK-N-SH cells alone (control) or together with 1 $\mu$M morphine during a 12 hour pretreatment period, followed by washout, no recovery period, and the cAMP assay (see Table 1), to establish the three cAMP values and thereby determine the spontaneous and naloxone induced cAMP overshoot. In a second set of experiments, the test compounds (10–100 $\mu$M) were added to the culture medium during a 30 minute or two hour recovery period. The first set of experiments was designed to identify agents that prevent the naloxone cAMP overshoot (i.e., prevent formation of the active $\mu^*$ state), whereas the second set of experiments was designed to identify agents that reverse the constitutive $\mu$ receptor activation in a short time period.

Among the compounds tested, H7 (1-(5-isoquinolinesulfonyl)-2-methylpiperazine dihydrochloride (10 and 100 $\mu$M)) abolished the naloxone cAMP overshoot when added together with the morphine pretreatment for 12 hours, followed by complete removal of both morphine and H7 drugs. In contrast, H7 pretreatment for 12 hours did not prevent the acute depression of cAMP levels by morphine, showing that it does not interfere with the agonist induced activation of the resting $\mu$ receptor state. Furthermore, when added immediately after the 12 hour morphine pretreatment period, during a recovery period of 30–120 minutes, H7 completely reversed the naloxone cAMP overshoot, i.e. it reversed the constitutively active $\mu^*$ state to the resting A state. Other compounds identified as protein kinase inhibitors capable of preventing formation of the constitutively active $\mu$ receptor state are H9 (N-(2-aminoethyl)-5-isoquinolinesulfonamide dihydrochloride) and HA-1004 (N-(2-guanidinoethyl)-5-isoquinolinesulfonamide hydrochloride).

H7 is known to inhibit several protein kinases including PKA and PKC. H7 is a representative of a class of compounds which could prevent and reverse long term narcotic effects by preventing the formation of the constitutively active $\mu$ receptor state but without blocking acute effects. This type of compound may be useful in enhancing the clinical use of narcotic analgesics or in treating narcotic addiction.

EXAMPLE 2

Another focus in practicing the inventive screening is to locate an opioid null antagonist with no ability to reverse the constitutively active $\mu$ opioid receptor state. Whereas naloxone is considered a $\mu$ opioid antagonist (i.e., blocking the activation of the $\mu$ receptor), it is also an inverse agonist, as defined here (i.e., blocking the constitutively active receptor) and illustrated earlier. Hence, its ability to cause severe and immediate withdrawal symptoms is high.

Using SK-N-SH cells, pretreated with 1 $\mu$M morphine for 12 hours, CTOP (D-Phe-Cys-Tyr-D-Trp-Arg-Thr-Pen-Thr-NH$_2$) (1 $\mu$M) was found not to reverse the constitutive activity of the $\mu$ receptor state (i.e., it does not cause the naloxone cAMP overshoot), whereas it has previously been known to fully block the acute effects of morphine. In the inventive cAMP assay system, such a compound is now shown to block the acute effects of morphine, as expected from an antagonist at the resting $\mu$ receptor state, but will also block the inverse agonist effects of naloxone.

To test for these properties of CTOP in the inventive assay, SK-N-SH cells were pretreated for 12 hours with 1 $\mu$M morphine (or with no drug as control) to establish the first and second cAMP values, with no recovery period before the cAMP assay (see Table 1). Then naloxone was replaced by CTOP (1–10 $\mu$M) to determine the third cAMP value. Since the second and third cAMP values were not different, CTOP does not act as an inverse agonist as does naloxone. To test whether CTOP blocks the effects of naloxone, CTOP (1–10 $\mu$M) and naloxone (0.1–1 $\mu$M) were added in combination to the cAMP assay. Reversal of the naloxone cAMP overshoot showed CTOP to act as a neutral (null) antagonist at the active $\mu^*$ state. Further, CTOP (1–10 $\mu$M) also reversed the reduction of the cAMP level caused by morphine (1 $\mu$M), confirming it to act as an antagonist at the resting $\mu$ state. Similar results were obtained with CTOP analog CTAP (D-Phe-Cys-Tyr-D-Trp-Arg-Thr-Pen-Thr-NH$_2$).

The selective $\mu$ antagonist CTOP, with a structure completely different from naloxone, is thus a prototypic example of a null antagonist of the $\mu$ receptor, having no effect on the constitutively active $\mu$ receptor state. The potential use of such a null antagonist is twofold. First, it could serve as an antagonist given clinically to counteract narcotic over-dose, with the advantage over naloxone that immediate severe withdrawal is avoided (assuming that withdrawal results to a large degree from reversal of the constitutive $\mu$ receptor activity). Second, null antagonists may also be useful in treating or inducing treatment of narcotic addiction, for example, in combination with a compound such as H7, to block the vicious circle of the dependent state.

Referring again to FIG. 1, the peptide $\mu$ opioid antagonist CTOP is shown here to act as a null or neutral antagonist at the $\mu^*$ receptor. Therefore, CTOP not only blocks the effects of the agonist morphine at the $\mu$ state, but also the effects of the inverse agonist naloxone at the activated $\mu^*$ state. The therapeutic potential of neutral antagonists is illustrated by the experiment showing CTAP causing significantly less withdrawal in morphine dependent mice and further reduced naloxone induced withdrawal.

Further applications for practice of the invention are to locate narcotic drugs with self-limiting maximal activity. Several narcotic agents display bell-shaped dose-response curves. These drugs produce maximal effects at an intermediate dosages level, and at higher doses reverse their own effects. The mechanism of this behavior of opioid drugs is unknown. Partial agonists at the $\mu$ receptor could at high doses also act as inverse agonists at the constitutively activated $\mu$ receptor, thereby blocking their own effects. The potency of the agonist and inverse agonist properties must be balanced such that sufficient acute effects are attained, and maximal effects, associated with respiration depression, are blunted.

Target compounds as safe analgesics are $\mu$ (partial) agonists with sufficient potency and efficacy at the constitutively active $\mu$ receptor to limit maximal response and side effects such as respiratory depression. Buprenorphine, a clinically used analgesic, is a prototypic example of such a compound although its self limiting properties are insufficient to prevent respiratory depression and addiction liability. Null antagonists acting at the constitutively active μ receptor only identified in this fashion could also serve in combination with conventional agonists to minimize peak effects or limit the duration of action.

EXAMPLE 3

The proposed model of narcotic tolerance and dependence should be a general phenomenon, applicable to all tissues containing the μ opioid receptor. The guinea-pig ileum is one of the most widely used in vitro tissue preparations, where narcotic agonists inhibit electrically induced twitching, as the functional endpoint. Exposure to morphine (24 hours) produces a dependent state which is characterized by naloxone induced twitching (after morphine has been completely removed). This naloxone induced twitching response is the equivalent to the naloxone cAMP overshoot in morphine pretreated SH-SY5Y cells.

The guinea-pig ileum was used to test the effects of kinase inhibitors and neutral antagonists. As predicted from the proposed mechanism of $\mu^*$ formation, brief treatment with H7 (50 μM for 10 minutes) largely suppressed naloxone induced twitching in the dependent guinea-pig ileum, suggesting prevention of $\mu^*$ formation. These results were predicted from the behavior of these compounds in SH-SY5Y cells, providing strong evidence for the notion that constitutive activation of the μ receptor is crucial to the dependent state. Further, organ tissues such as the guinea-pig ileum, or the mouse vas deferens, are also suitable for screening anti-addictive agents, such as kinase inhibitors and neutral antagonists.

EXAMPLE 4

Recently, several laboratories have cloned the μ receptor gene (e.g. Chan et al., *Molec. Pharmacolo.*, 44, 8–12 (1993)). We have stably transfected the μ gene into U293 cells (U293-μ~$10^6$ sites/cell), for a more convenient and definitive detection of $\mu^*$ activity for use as a screen for anti-addictive agents. Morphine pretreatment and washout of the drug were the same as described for Sh-SY5Y cells. Stimulation of cAMP accumulation in this case was best done with 10 μM forskolin for 10 minutes. Under these conditions, there was a measurable spontaneous cAMP overshoot after morphine pretreatment; however, the addition of 1–10 μM naloxone caused a very large additional increase in cAMP levels (up to about 500–600% = naloxone cAMP overshoot, IC:50, 1–3 nM), which indicates the presence of substantial $\mu^*$ activity suppressing cAMP levels.

These results show that the narcotic tolerant-dependent state can be reproduced in transfected non-neuronal cells, which can therefore serve as an attractive screening method for identifying anti-additive drugs.

It is to be understood that while the invention has been described above in conjunction with preferred specific embodiments, the description and examples are intended to illustrate and not limit the scope of the invention, which is defined by the scope of the appended claims.

It is claimed:

1. An in vitro assay useful in screening test compounds for effects on opioid μ receptors comprising:

providing intact cells having opioid μ receptors, the receptors being coupled to a cAMP production system under cell growth conditions and including an adenylyl cyclase stimulating agent;
(1) incubating a first portion of the receptors for about 12 hours or longer with a narcotic analgesic that functions as an agonist therein and forming a constitutively active receptor state;
(2) removing substantially all of the agonist from the receptor and determining a cAMP value while in the constitutively active state, but being substantially free of agonist molecules;
(3) determining another cAMP value by measuring cAMP production of a second portion of the receptors while being in the constitutively active state, being substantially free of any agonist molecules, but while being in the presence of naloxone as an inverse agonist to associate naloxone molecules with substantially all the receptors; and, adding a test compound to a third portion of receptors when in a constitutively active receptor state during incubation with narcotic analgesic or after removal thereof to screen for effects of the test compound on opioid μ receptor activity and measuring any cAMP changes resulting therefrom.

2. The assay as in claim 1 wherein the screening includes determining whether the test compound prevents or reverses the constitutively active μ receptor state.

3. The assay as in claim 2 wherein the cells are SK-N-SH or U293 where the μ gene has been transfected therein, and the adenylyl cyclase stimulating agent is forskolin.

4. The assay as in claim 1 wherein the cells are SK-N-SH or U293, transfected with the μ opioid receptor gene and the test compound is classified based on an ability to change constitutive μ receptor activation.

5. The method as in claim 1 wherein the narcotic analgesic is morphine.

* * * * *